United States Patent
Houston et al.

(10) Patent No.: US 11,896,522 B2
(45) Date of Patent: Feb. 13, 2024

(54) ACTIVE MAGNETIC PROSTHESIS FOR EYE-LID RE-ANIMATION

(71) Applicant: The Schepens Eye Research Institute, Inc., Boston, MA (US)

(72) Inventors: Kevin Houston, Boston, MA (US); Eleftherios Paschalis Ilios, Boston, MA (US); Matteo Tomasi, Boston, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 1149 days.

(21) Appl. No.: 16/607,143

(22) PCT Filed: Apr. 27, 2018

(86) PCT No.: PCT/US2018/029863
§ 371 (c)(1),
(2) Date: Oct. 22, 2019

(87) PCT Pub. No.: WO2018/200994
PCT Pub. Date: Nov. 1, 2018

(65) Prior Publication Data
US 2020/0383831 A1 Dec. 10, 2020

Related U.S. Application Data

(60) Provisional application No. 62/491,983, filed on Apr. 28, 2017.

(51) Int. Cl.
*A61F 9/007* (2006.01)
*H01F 7/02* (2006.01)
(Continued)

(52) U.S. Cl.
CPC .......... *A61F 9/00718* (2013.01); *A61N 2/006* (2013.01); *A61N 2/02* (2013.01);
(Continued)

(58) Field of Classification Search
CPC ...... A61N 2/00–12; A61H 5/00; A61H 5/005; A61F 9/00; A61F 9/0026; A61F 9/00718; H01F 7/02; A61B 2017/00539
See application file for complete search history.

(56) References Cited

U.S. PATENT DOCUMENTS 3,923,044 A * 12/1975 Miller ..................... A61F 9/007
351/158
5,823,938 A * 10/1998 Hernandez .............. A61F 9/007
600/15
(Continued)

OTHER PUBLICATIONS

International Search Report and Written Opinion issued in International Patent Application No. PCT/US2018/029863 dated Jul. 9, 2018.
(Continued)

*Primary Examiner* — Valerie L Woodward
(74) *Attorney, Agent, or Firm* — Quarles & Brady LLP

(57) ABSTRACT

A device includes a frame, a rotatable housing and a permanent magnet. The frame is configured to be worn adjacent an eye region of a wearer. The rotatable housing is coupled to the frame. The permanent magnet is coupled to the rotatable housing and includes a first surface having a first static magnetic polarity and a second surface having a second static magnetic polarity opposite the first static magnetic polarity. The rotatable housing is arranged to rotate the permanent magnet between a first position orienting the first surface towards the eye region of the wearer and a second position orienting the second surface towards the eye region of the wearer. Related apparatus, systems, techniques and articles are also described.

19 Claims, 8 Drawing Sheets

(51) Int. Cl.
*A61N 2/02* (2006.01)
*A61N 2/00* (2006.01)
*A61N 2/06* (2006.01)
*A61B 17/00* (2006.01)
*A61F 9/00* (2006.01)

(52) U.S. Cl.
CPC ................. *A61N 2/06* (2013.01); *H01F 7/02* (2013.01); *A61B 2017/00539* (2013.01); *A61F 9/00* (2013.01); *A61F 9/0026* (2013.01)

(56) References Cited

U.S. PATENT DOCUMENTS

| | | | |
|---|---|---|---|
| 2005/0213034 A1* | 9/2005 | Nagayoshi | A61H 5/00 351/203 |
| 2006/0069420 A1* | 3/2006 | Rademacher | A61N 2/06 607/141 |
| 2009/0112207 A1 | 4/2009 | Walker et al. | |
| 2013/0274541 A1* | 10/2013 | Lipson | A61N 2/06 600/15 |

OTHER PUBLICATIONS

De Negreiros WA, et al., "Surgical and prosthetic considerations to rehabilitate an ocular defect using extraoral implants: a clinical report", Journal of Prosthodont 21, 2012, 205-208.

FDA, "510(k) Summary of Safety and Effectiveness, Tegaderm, 3M Medical Products Division", Food and Drug Administration, 1997, Entire document.

Ganz RA, et al., "Esophageal sphincter device for gastroesophageal reflux disease", The New England Journal of Medicine, 2013, 368;8 : 719-727.

Houston KE, et al., "A Prototype External Magnetic Eyelid Device for Blepharoptosis", Transl Vis Sci Technol, 2014, vol. 3, article 9.

Paschalis EL, et al., "A novel implantable glaucoma valve using ferrofluid", PloS one, 2013, vol. 8, Issue 6: e67404. doi: 67410. 61371/journal.pone.0067404.

Senders, et al., "Force requirements for artificial muscle to create an eyelid blink with eyelid sling", Archives of Facial and Plastic Surgery, 2010, vol. 12:30-36.

* cited by examiner

Tegaderm Over Array After 30 min.

| Table: Individual data for adjustable force active system testing in human subjects. 30 degrees of angular translation resulted in clinically significant change in lid position (> 1mm) in 75% of subjects, with an average of 2.45mm | | | |
|---|---|---|---|
| Subject | Lid Opening (mm) at 0 degrees rotation angle | Lid Opening (mm) at 30 degrees rotation angle | Difference |
| 1 | 1.92 | 2.37 | 0.45 |
| 2 | 5.93 | 8.84 | 2.91 |
| 3 | 10.00 | 14.00 | 4.00 |
| 4 | 5.7 | 7.54 | 1.84 |
| Mean | | | 2.45 |
| SD | | | 1.48 |

ACTIVE MAGNETIC PROSTHESIS FOR EYE-LID RE-ANIMATION

CROSS-REFERENCE TO RELATED APPLICATIONS

This application is a national stage application, filed under 35 U.S.C. § 371, of International Application No. PCT/US18/29863 filed on Apr. 27, 2018, which claims priority under 35 U.S.C. § 119 to U.S. Provisional Application No. 62/491,983, filed Apr. 28, 2017, the contents of each of which are hereby incorporated by reference in their entirety.

STATEMENT REGARDING FEDERALLY SPONSORED RESEARCH

This invention was made with government support under EY016335 awarded by the National Institutes of Health. The government has certain rights in the invention.

TECHNICAL FIELD

The subject matter described herein relates to mechanically opening and closing the eye.

BACKGROUND

There are currently limited or no available non-surgical treatments for patients with bidirectional paralysis of eye lid motility that re-animate the lid. Surgical treatments are limited. Bi-directional paralysis of eye lid motility results in exposure of the eye, desiccation of the cornea, loss of epithelial barrier, which can result in pain, exposure keratopathy, infections, de-innervation of the cornea, blurred vision, and eventually scarring and corneal melting. One way to prevent this is copious use of ocular lubricants. However, exposure and evaporative forces over extended periods of time can eventually lead to scarring, visual impairment or even corneal blindness.

Another way to protect the ocular surface is to partially suture the eye lids closed (Lateral Tarsorrhaphy). This has limitations of reduced peripheral field of vision and tear pooling which degrades and distorts vision.

SUMMARY

In an aspect, a device includes a frame, a rotatable housing and a permanent magnet. The frame is configured to be worn adjacent an eye region of a wearer. The rotatable housing is coupled to the frame. The permanent magnet is coupled to the rotatable housing and includes a first surface having a first static magnetic polarity and a second surface having a second static magnetic polarity opposite the first static magnetic polarity. The rotatable housing is arranged to rotate the permanent magnet between a first position orienting the first surface towards the eye region of the wearer and a second position orienting the second surface towards the eye region of the wearer.

One or more of the following features can be included in any feasible combination. The device can further include a servo motor, a stepper motor, a linear motor, a micro-fluidic motor, a hydraulic motor, or a knob. A micromagnetic array can be adhered to an eyelid of the wearer and surrounded by an optically clear polymer. The permanent magnet can include a neodymium magnet. The optically clear polymer can include a silicon-based organic polymer. The optically clear polymer can include polydimethylsiloxane (PDMS). A memory controller unit can be coupled to a motor and can include a memory and a controller. The controller can be configured to access a predetermined rotation schedule protocol included in the memory and to control the rotation of the permanent magnet based on the predetermined rotation schedule protocol. The predetermined rotation schedule protocol can include instructions to actuate the motor every 2 seconds, every 3 seconds, every 4 seconds, every 5 seconds, every 6 seconds, every 7 seconds, every 8 seconds, every 9 seconds, every 10 seconds, every 11 seconds, every 12 seconds, every 13 seconds, every 14 seconds, every 15 seconds, every 16 seconds, every 17 seconds, every 18 seconds, every 19 seconds, every 20 seconds, every 10 hours, or every 20 hours. An input can be coupled to the rotatable housing and configured to control the rotation of the permanent magnet when the input is activated by a user. The input can include a button, a knob, or a switch.

In another aspect, a method is provided. The method includes providing a frame configured to be worn adjacent an eye region of a wearer, a rotatable housing coupled to the frame, and a permanent magnet coupled to the rotatable housing and including a first surface having a first static magnetic polarity and a second surface having a second static magnetic polarity opposite the first static magnetic polarity, the rotatable housing arranged to rotate the permanent magnet between a first position orienting the first surface towards the eye region of the wearer and a second position orienting the second surface towards the eye region of the wearer. The method includes actuating a micromagnetic array adhered to an eyelid of the wearer by rotating the permanent magnet between the first position and the second position to move the eyelid.

One or more of the following features can be included in any feasible combination. For example, the method can include providing a servo motor, a stepper motor, a linear motor, a micro-fluidic motor, a hydraulic motor, or a knob. The micromagnetic array can include a magnet surrounded by an optically clear polymer. The permanent magnet can include a neodymium magnet. A memory controller unit can be coupled to a motor and can include a memory and a controller. The controller can be configured to access a predetermined rotation schedule protocol included in the memory and to control the rotation of the permanent magnet based on the predetermined rotation schedule protocol. The method can include providing an input coupled to the rotatable housing and configured to control the rotation of the permanent magnet in response to activation of the input by a user. The input can be a button, a knob, or a switch. The micromagnetic array can be adhered to the eyelid of the wearer using a hydrocolloid adhesive provided over a top surface of the micromagnetic array. The predetermined rotation schedule protocol can include instructions to actuate the motor every 2 seconds, every 3 seconds, every 4 seconds, every 5 seconds, every 6 seconds, every 7 seconds, every 8 seconds, every 9 seconds, every 10 seconds, every 11 seconds, every 12 seconds, every 13 seconds, every 14 seconds, every 15 seconds, every 16 seconds, every 17 seconds, every 18 seconds, every 19 seconds, every 20 seconds, every 10 hours, or every 20 hours.

Non-transitory computer program products (i.e., physically embodied computer program products) are also described that store instructions, which when executed by one or more data processors of one or more computing systems, causes at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

Like reference symbols in the various drawings indicate like elements.

DETAILED DESCRIPTION

The current subject matter can include an approach to mechanically close the eyelid for patients suffering from eyelid paralysis. In some implementations an eyeglass frame (e.g., glasses) can include a permanent magnet. The magnet can be attached to the frame such that it can be rotated. When another magnet is attached (e.g., via adhesive or surgical implantation) to an eyelid of a wearer, a magnetic field generated by the permanent magnet can interact with a magnetic field generated by the magnet attached to the eyelid to create a force on the eyelid. The force can, depending on the orientation of the permanent magnet, cause the eyelid to open (e.g., via an attraction force) or close (e.g., via a repellant force). Such an approach can be used to re-animate a fully or partially paralyzed eyelid and serve as a treatment or rehabilitation aid for individuals suffering from forms of Blepharoptosis, Lagophthalmos, or both (total eyelid paralysis). In some implementations, by utilizing a permanent magnet on the frame, the size and weight of the device can be reduced and overheating, which may occur with an electromagnet, can be avoided. In some implementations, the permanent magnet can be rotated manually or via a motor, which can be controlled by a controller to enable automatic blinking as may be needed in cases of total paralysis.

The current subject matter can enable mechanically opening and closing the eye in patients suffering from eyelid paralysis. This can be used to re-animate a completely paralyzed eye lid by mechanically opening and closing the eye every few seconds. When the device is used for ptosis (paralysis of eye opening, but eye closing is intact) it can be referred to as the Magnetic Levator Prosthesis (MLP), since the magnetic force provides the force normally generated by the muscle of eyelid opening (Levator Palpebrae Superioris). For the treatment of ptosis, the active system feature can allow doctors and patients to manually rotate and thereby adjust the force of the MLP to meet their needs in the interest of maximizing their comfort and blink quality while accommodating variability in ptosis or lid magnet array positioning (which can vary hourly). Rotation of the permanent magnet can used to increase or decrease the attractive force between the permanent magnet and eye lid magnet array to provide a self-customized amount of force (there is no polarity reversal). Rotation of the permanent magnet can be performed manually.

Figure 1:
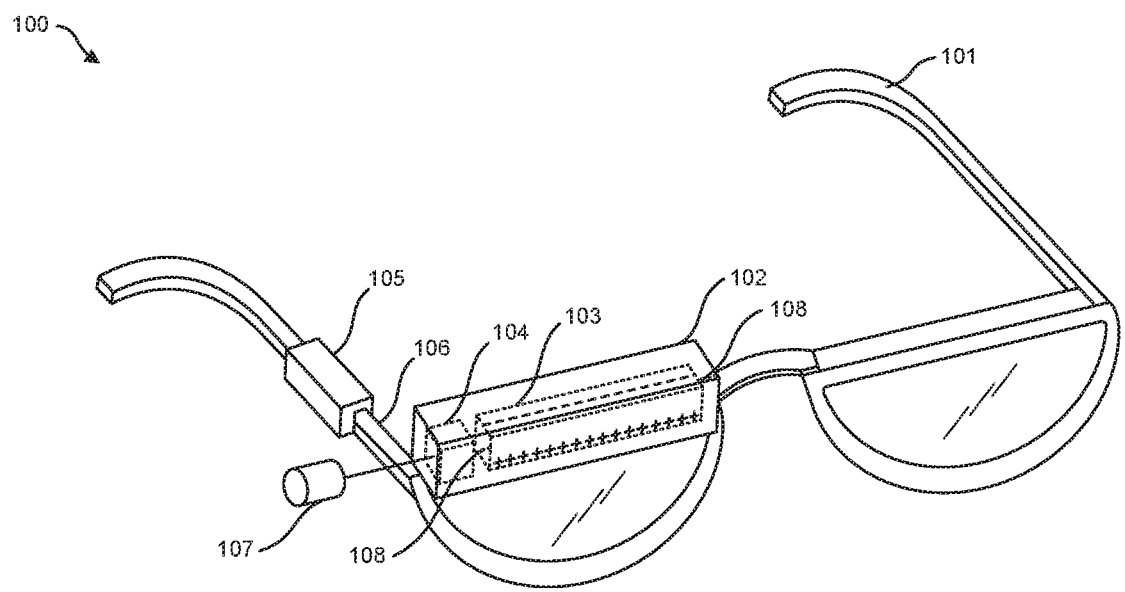
FIG. 1 is a representation of an example device for mechanically opening and closing an eyelid.

FIG. 1 is a representation of an example device 100 for mechanically opening and closing an eyelid. The device can include a frame 101, for example, of a spectacle or eyeglass, onto which a rotatable housing 102 can be attached or integrated. A permanent magnet 103 can be coupled to the rotatable housing 102 and can also be coupled to a motor 104. The device can further include a memory controller unit 105 that can be mounted to the frame 101 and coupled to the motor 104 by a connector 106. The memory controller unit 105 can be configured to actuate the motor and thereby rotate the permanent magnet 103. In some implementations, the memory controller unit 105 can be separate from the frame 101 and stored, for example, in the pocket of the user. In some implementations, the memory controller unit 105 can be wirelessly connected to the motor 104 instead of by connector 106. In this exemplary embodiment, the device includes an input 107 coupled to the motor 104 and the permanent magnet 103 that can allow the user to manually rotate the permanent magnet 103 by hand. The input can be a knob, a button, or a switch.

The frame 101 can include an eyeglass frame that is configured to be worn adjacent an eye region of a wearer. A variety of spectacle types and designs can be used in the device, however in some implementations the frame 101 can support the weight of the other components of the device. In some implementations, the device can be adhered to the forehead/brow region, or it can be held in place by a ball cap or head band, and need not be in the form of eyeglass frames.

In some implementations, the permanent magnet 103 can include a ½×½ inch neodymium-52 (NdFeB) cylinder or other permanent magnet of similar size, grade or shape, (e.g. sphere) magnetized perpendicular to the axis of rotation, mounted on an axon 108, which can be any flexible material. The permanent magnet 103 can include a first surface having a first static magnetic polarity and a second surface having a second static magnetic polarity opposite the first static magnetic polarity. The axon 108 can be coupled to the motor 104 and to the input 107 on a first end. The axon 108 can be coupled to the rotatable housing 102 on a second end. The motor 104 can be, for example, a servo motor, a stepper motor, a linear motor, a micro-fluidic motor, a hydraulic motor, or any other kind of motor that provides rotational output.

The memory controller unit 105 can include a controller 105a and a memory 105b. The memory controller unit is connected to the motor 104 via a connector 106, which can transmit actuation instructions from the memory controller unit 105 to the motor 104. The controller 105a can be configured to access a predetermined rotation schedule protocol included in the memory 105b and to control the actuation of the motor 104, and therethrough the rotation of the permanent magnet 103, in accordance with the predetermined rotation schedule protocol. The predetermined rotation schedule protocol can instruct the controller 105a to actuate the motor 104 to rotate the permanent magnet 103 at a preferred interval so as to simulate blinking. In some implementations, the predetermined rotation schedule protocol can include instructions to actuate the motor 104 every 2 seconds, every 3 seconds, every 4 seconds, every 5 seconds, every 6 seconds, every 7 seconds, every 8 seconds, every 9 seconds, every 10 seconds, every 11 seconds, every 12 seconds, every 13 seconds, every 14 seconds, every 15 seconds, every 16 seconds, every 17 seconds, every 18 seconds, every 19 seconds, or every 20 seconds; or, every 10 hours, or every 20 hours.

In operation, a user can place the frame 105 adjacent to the user's eyelid and can initialize the permanent magnet 103 by rotating the input 107 such that the magnetic force between a micromagnetic array adhered to the eyelid of the user (as explained in further detail below) and the permanent magnet 103 can be magnetically interactive. The memory controller unit 105 can then be activated, and, once activated, the memory controller unit 105 can issue a command to the motor 104 to periodically rotate the axon 108; since the axon 108, the motor 104, and the permanent magnet 103 are all coupled together and therefore rotate in unison, the permanent magnet 103 can be correspondingly rotated by the motor 104. A magnetic field generated by the permanent magnet 103 can interact with a magnetic field generated by the micromagnetic array to create a force on the eyelid. The force can, depending on the orientation of the permanent magnet, cause the eyelid to open (e.g., via an attraction force) or close (e.g., via a repellant force). Alternatively, since input 107 can also be coupled to axon 108, and therefore coupled to permanent magnet 103, the user can override the operation of motor 104 by rotating the input 107 by hand, thereby achieving the same magnetically-induced eyelid movement that the operation of motor 104 can provide. Additionally, the user can rotate input 107 to adjust the position of the permanent magnet 103 and thereby change the amount of magnetic interaction between the permanent magnet 103 and the micromagnetic array to adjust the amount of force applied to the eyelid by changes in ptosis severity or the positioning of the frame 101.

In some implementations, the current subject matter can include a magnetic device that can correct bidirectional paralysis of eyelid motility. It can be used to treat unidirectional ptosis or lagophthalmos. The device can include an array of permanent micromagnets embedded in a biocompatible elastomer that is attached to the upper eye-lid, and a secondary rotational magnet mounted on the frame.

The current subject matter can include a device that can reverse the polarity of the secondary frame magnet by rotation of a static magnet and hence can cause blinking. This can simplify the manufacturing process and provides the ability to customize the parameters of the blinking to individual patient's needs. This example device can also enable for unidirectional correction of eye lid motility. A change of rotation rate can make the device correct ptosis or lagophthalmos (e.g., reverse polarity every 1 day for 1 sec). The device can adapt to different blinking needs. In order to re-animate the eye lid in bi-directional paralysis, the force on the lid can rapidly reverse its direction. There can be need to control the magnitude of the force and the trajectory during blinking, because failure to do so could result in injury to the user. Analysis has been performed and a force vector on an eyelid of a user has been modeled to allow better control of the magnitude and trajectory of the blinking and the apposition of the lid margin to the ocular surface.

Newer classes of permanent magnets can make a rotary static magnet system for eye lid paralysis feasible. For example, today's Neodymium magnets can generate up to 1.3 T (Teslas) compared to 0.4 T of conventional ferrite magnets. Neodymium magnets have exceptional uniaxial magnetocrystalline anisotropy, which makes them resistive to demagnetization. The increased magnetic force at a fraction of the size has led to attempts for other medical applications including implantation for gastroesophageal reflux disease, dental prosthetics, ocular reconstructive surgery, and glaucoma.

Data shows that an example implementation of the current subject matter can generate adequate force to perform lid reanimation in patients. Previous attempts to reanimate the lid were based on electro-magnets or piezo-electrical polymer systems. However, all these designs were energy inefficient and in many cases generated significant heat making the system impractical.

Figure 2:
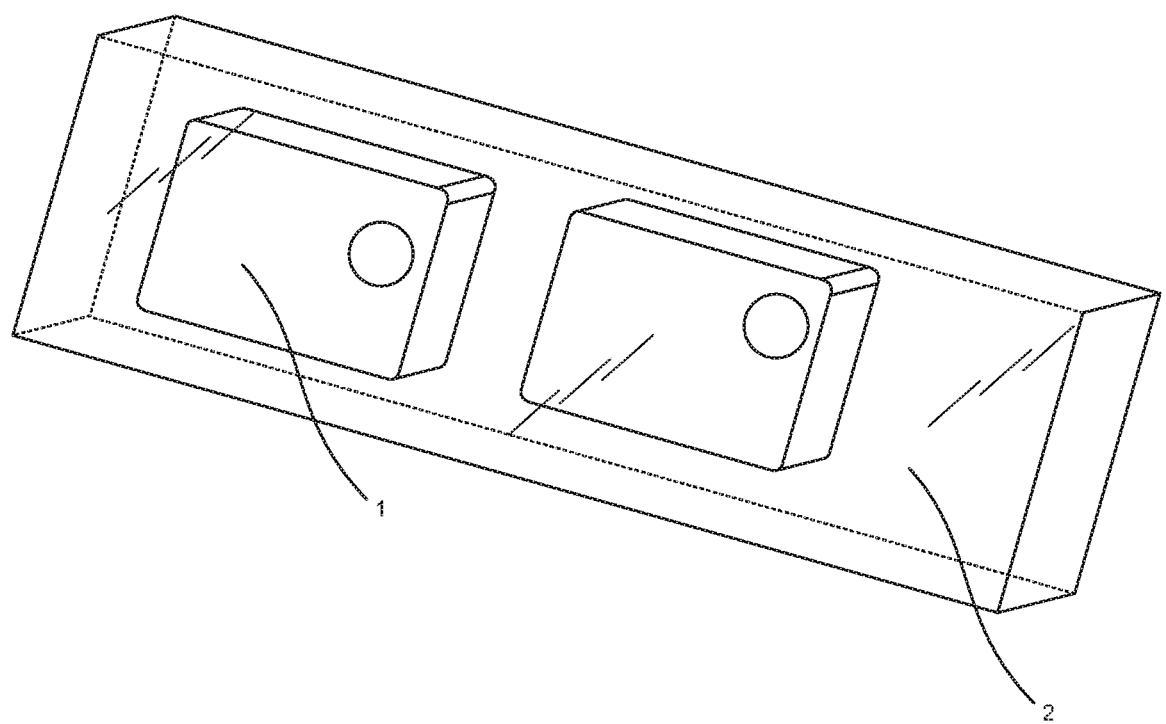
FIG. 2 illustrates a magnified view of an example of the lid magnet showing two micro-magnets (1) embedded in Polydimethylsiloxane (PDMS) (2), a soft, flexible, bio inert polymer.
Figure 3:
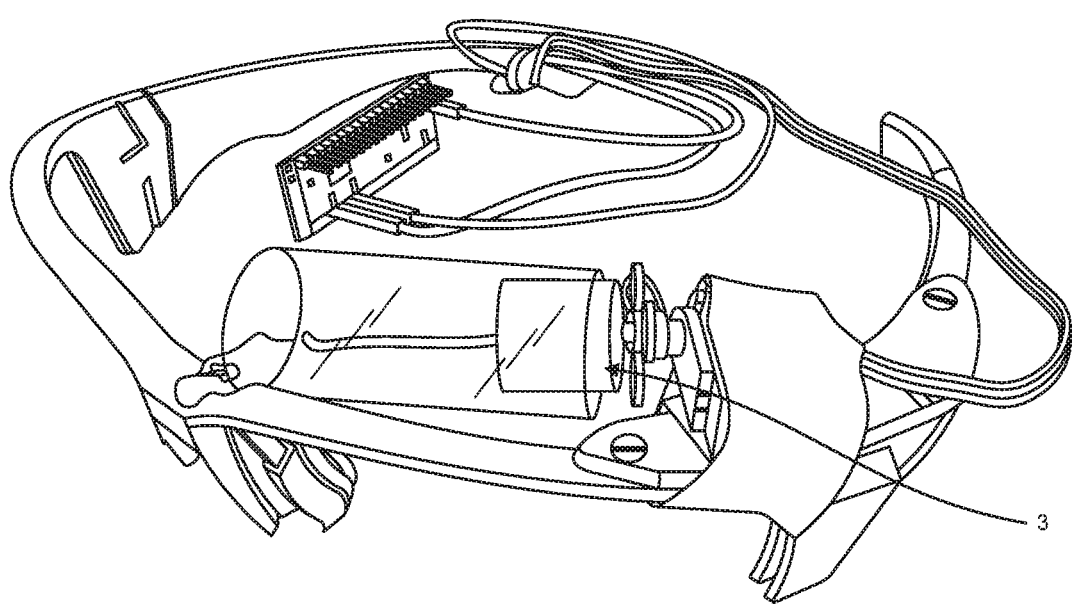
FIG. 3 is a photo illustrating an example frame mounted portion of the rotary magnet device (½ in. neodymium cylindrical magnet), with a servo mounted along the temple, according to some implementations. Components can be encased and attached to the eye wire.

In an example implementation, there is shown in FIG. 2 a micro-magnet array showing 2×3×1 mm neodymium cubes (1) and flexible bioinert elastomer (2). Some implementations of the device can enable positional changes of a spectacle magnet that cause significant attraction and repulsive magnetic force and lid movement. A motor can rotate the secondary spectacle magnet (3), as shown in FIG. 3, and this arrangement can be very efficient and feasible. When poles of two magnets are opposite, an attractive force is generated that lifts the lid upward (open). When the poles are identical, a repulsive force is generated pushing the lid downward (closed).

Figure 5A:
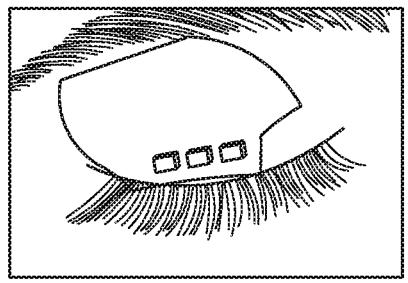
FIG. 5A is a photograph illustrating proper placement of an example array with eye closed (top left).
Figure 5B:
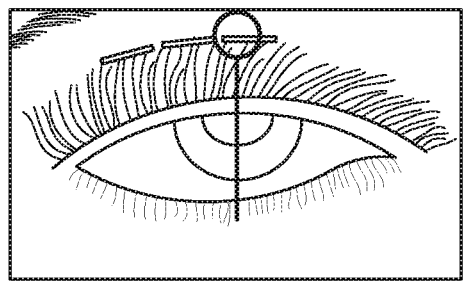
FIG. 5B is a photograph illustrating proper placement of the example array with eye open (wearing magnet frames). The first magnet is positioned approximately directly above the center of the pupil. The whole array is decentered out (closer to the ear than the nose). Magnetic lid array showing positioning on the lid and when closing the eye when wearing the device for ptosis. The array is decentered slightly outwards with the first (nasal-most) magnet in-line with the pupil.
Figure 5C:
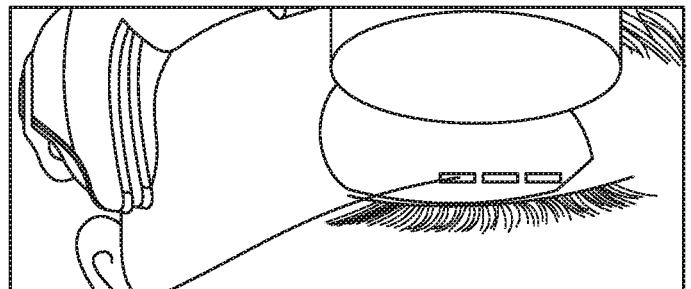
FIG. 5C is a photograph illustrating an example array with eye closed, 30 minutes after application of Tegaderm over the array.
Figure 6A:
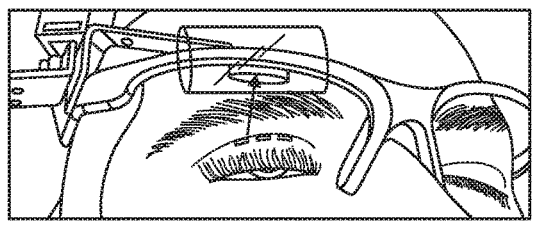
FIGS. 6A-6C illustrates sequential video frames from an example device showing automated blinking.
Figure 6B:
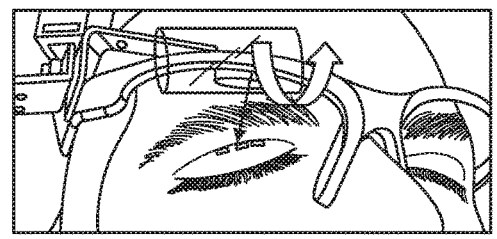
Figure 6C:
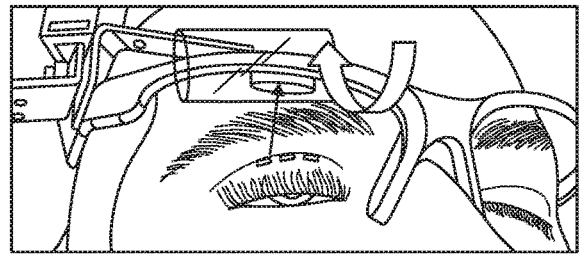

In an example implementation, the device can include a micromagnetic array that attaches to the eyelid, as shown in FIGS. 5A-5C. The micromagnetic array may include at least one eyelid magnet, for example, it may include three or more eyelid magnets. Additional numbers of magnets are possible. The eyelid magnets are produced by embedding permanent (e.g., NdFeB N-52) micro-magnets (e.g. ⅛ in×⅛ in) in a soft flexible bio-inert polymer such as polydimethylsiloxane (PDMS)(FIG. 2). PDMS is an example of a silicon-based organic class of polymers. PDMS is optically clear, and, in general, inert, non-toxic, and non-flammable. It is also called dimethicone and is one of several types of silicone oil (polymerized siloxane). Other types of inert elastomers can be used, such as Neoprene (Chlorpren), Nitrile-Buna-N, Styrene Butadiene, Natural Rbber (pure gum amber), Ethylene Propylene-Diene Monomer, Hypalon, Silicon Rubber, Viton, Butyl (Isoprene), Urethane sheet, C.I. Rubber, SIMRIZ®, AFLAS®, Carboxilated Nitrile, DUPONT VITON®, Fluorosilicone, Highly Saturated Nitrile, Nitrile (Buna-N), Nitrile (Low-Temp), Polyurethane, FEP, Polyacrylate, Silicone polyhydromethylsiloxane (PHMS), polymethylphenylsiloxane (PMPhS), fluorosilanes, and copolymers of silicone-acrylates, polyether polysiloxane and fluorinated acrylates. The magnets are separated by the flexible bio-inert polymer (e.g., PDMS), providing a flexible strip that conforms to the lid shape. In addition, this allows on-demand trimming of the strip (using scissors or artist's knife) and adjustment of the magnetic force according to the severity of the paralysis. The strip may be curved to match the contour of the eyelid.

The eyelid magnets can be produced by embedding permanent NdFeB micro-magnets (typically ⅛ in×⅛ in) in polydimethylsiloxane (PDMS) biocompatible polymer or other elastomers using soft lithography techniques, 3D printing, mold injection techniques or other industrial fabrication techniques. The well-arranged polarization of the magnet arrays can create uniform magnetic force. The magnets can be separated by PDMS, thus providing a flexible strip that can conform to the lid shape. In addition, this can allow on-demand trimming of the strip (using scissors or artist's knife) and adjustment of the magnetic force according to the condition.

The PDMS micromagnetic array can be attached to the lids by draping Tegaderm or IV-3000 or similar adhesive over the top of the array. A commercially available double-sided skin adhesive marketed for the attachment of external lid weights (EyeClose®) was insufficient to maintain adhesion of the example magnet array for more than an hour or two, whereas Tegaderm remained adhered for 3-5 days. Thanks to its extremely thin, transparent characteristics, Tegaderm was preferred by participants over another medical adhesive tested during prototype development (i.e., Transpore, 3M, St. Paul Minn.). Other adhesives may be used.

The micromagnet array can be attached to the lids using common medical skin adhesives, most commonly hydrocolloid based material such as Tegaderm (3M, St. Paul, MN.) or IV-3000. Hydrocolloid adhesives are commonly used for IV catheter securement, wound dressing, and occasionally as a protective eye covering. Hydrocolloids can be extremely thin, transparent, and oxygen permeable with an established safety profile for days to weeks of wear. The hydrophilic properties are beneficial on the eyelids, which are often moist.

In some implementations, proper application of the adhesive and magnet array to the eyelid can include trimming a piece of Tegaderm or IV-3000 to a size just smaller than that of the upper eyelid of a patient and draping it over the top of the array. Part of the Tegaderm or IV-3000 backing can be preserved to aid in handling. The lids can be prepped prior to application with a warm wash cloth and an alcohol swab or lid scrub. The backing can be peeled halfway back and the Tegaderm or IV-3000-wrapped magnet placed on the adhesive side using non-metallic contact lens tweezers (Bernell Corp., Mishawaka Ind.). The micromagnetic array and Tegaderm or IV-3000 draping then be stuck on the lid close to the lashes. Contact lens tweezers can be used to lift out any lashes that may become trapped under the draping. The tweezers can further be used to gently press down the edges of the draping to form a tight bond with the eyelid. In some embodiments, the array can be glued directly to the eyelid using biocompatible polymer glue, cured in situ by light or other forms of catalysts. A Tegaderm or IV-3000-wrapped can be used. In other embodiments, the array can be permanently implanted into the eyelid, surgically.

Management of Bi-directional Eye Lid Motility Dysfunction: a group of conditions having multiple etiologies including but not limited to palsy of both CN 7 and CN III from trauma, tumor, autoimmune, or infectious causes; mechanical restriction such as scarring of the facial skin from injury, autoimmune conditions or burns, or structural damage to the orbit from trauma or other pathology.

Management Uni-directional Eye Lid Motility Dysfunction: while some implementations of the current device can be used to correct bi-directional paralysis, it can also be capable of treating unidirectional paralysis. A problem encountered with some available treatments that utilize magnets is over correction and lack of control over the force. For example, non-rotatable magnetic devices can overcorrect ptosis at the peak of eye opening, sometimes preventing a spontaneous blink. This can result in over exposure of the corneal surface where evaporative forces can eventually lead to corneal edema and pain and therefore failure of the treatment. The current bidirectional magnetic prosthesis, after opening the eye, allows the force to be reduced to match the natural spontaneous blink rate. There can be programmable blinking rate and frequency as well as control over the force and trajectory of the lid reanimation to address this issue. Appropriate blinking rates can include every 1, 2, 3, 4, 5, 6, 7, 8, 9, 10, 11, 12, 13, 14, 15, 16, 17, 18, 19, or 20 seconds, and appropriate forces can range from 1 g to 40 g. The rotatable permanent magnet allows easy adjustment of the force and trajectory required to lift the lid, which can be dependent upon the severity of ptosis and other biomechanical variables of the lid and orbital structure of individual patients. This can be true for correction of lagophthalmos, but the direction is opposite.

Available Ptosis Treatments and Limitations: include ptosis crutch, surgical intervention static non-rotatable magnet systems, and skin adhesives. Some devices act as a ptosis crutch, and have not achieved widespread use, at least because it physically props the eye open, has to be continually adjusted, does not allow a complete blink, and may abrade the cornea. Surgical intervention (Frontalis Sling) has been recommended and widely used for chronic ptosis, however is not appropriate in the weeks to months following neurological insult as the patient may recover partially or completely. Surgical treatments are often irreversible and allow little customization and/or control over the treatment course. Some patients are not candidates for surgery or decline surgery. Some static non-rotatable magnet systems can over correct the ptosis when high force close to the magnet surface prevents spontaneous blinking. Some therapists (OT, PT, SLP) attempt to use readily available skin adhesives (e.g., physiotape) to tape the eye open, however these may leave a portion of the eye continuously open, resulting in blur and eye pain from desiccation. Instructing the patient hold the lid open ties up one arm and further disables the patient.

Available Lagophthalmos Treatments and Limitations include lid weights and Tarsorrhaphy. Implantable lid weights are a treatment for lagophthalmos and may work fairly well in many cases. Limitations include: the need to have a surgical procedure to explant with irreversible change to the eye lid tissue (making them undesirable during the recovery phase), reverse effect when reclined, weights become bulky with increasing severity of the condition, sagging of the lower lid is not addressed, and poor efficacy with external mounting (e.g., Blinkeze external lid weights mounted with double sided adhesive, manufactured by Med-Dev).

But the amount of lid closure can be dependent upon the amount of weight. In general the weights can be large and can become bulky. At some point the weights reach a limit so that the most serious conditions cannot achieve full lid closure. Weights may only work when the patient is upright. When lying on their back, the weight actually facilitates eye opening. There is also paresis of the Orbicularis (lid muscles) of the lower lid. This sagging of the lower lid is not addressed by the weights, leaving the lower conjunctivae and inferior cornea exposed indefinitely.

Tarsorrhaphy includes suturing of the lateral ⅓ to ½ of the lids. While this is often effective to preserve the cornea, it is invasive, can be unsightly, and limits the visual field. Suturing of the lateral ⅓ to ½ of the eye lids provides partial coverage and tear pooling nasally to protect the ocular surface. This procedure is commonly used and easily reversible. But tarsorrhaphy is uncomfortable, requires surgery, and limits the visual field.

Magnetic tarsorrhaphy: External magnets can be non-surgically applied to the upper and lower lids providing an attractive force to pull the lids firmly for complete eye closure, which can be superior to weights alone. Lawrence G, Paschalis E I, Tomasi M, et al. A Non-Invasive Magnetic System for Temporary Management of Lagophthalmos-Proof of Concept (Abstract). Optom Vis Sci 2016; 93: E-abstract 16091. However they often are positioned very close to the lid margin to generate enough force for complete closure and using hydrocolloid adhesives, poor adhesion time (hours rather than days) has been a limitation. Lawrence G, Paschalis E I, Tomasi M, et al. A Non-Invasive Magnetic System for Temporary Management of Lagophthalmos-Proof of Concept (Abstract). Optom Vis Sci 2016; 93: E-abstract 16091. Use of magnetic repulsion is another approach which only requires a magnet on the upper lid in the same manner as done for ptosis. However a constant repulsive force can cause ptosis, and the current rotary system, which can modulate the force when closure is desired, providing programmable blink frequency, can be an improvement.

Example materials that can be used include, for the eye lid magnet array: ⅛ by×⅛ in. or similar size N52 NdFeB or similar material magnets (Distributed by e.g. K&J Magnetics, Pipersville, Pa.), PDMS based bioinert polymer, and tegaderm or similar medical grade adhesive (3M, St. Paul, Minn.); for the permanent magnet: frame with motor mounted and small battery component, ½" dia.×½" or similar size Nickel Plated N52 NdFeB magnet, cylinder or sphere (SM Magnetics, Pelham AL); and Power HD High-Speed Digital Sub-Micro Servo Motor DSP33 (e.g., www-.pololu.com), or similar.

Other technologies considered and the relative benefits of permanent magnets: the permanent magnets used in the example device are neodymium N52 (NdFeB), which are widely available, require no power source, and are inexpensive. However, other types of magnets made of different material that can over perform current magnets can be used. Electromagnets might both open and close the eye, but they are more expensive, require an external power source, and generate heat. Permanent magnets may not carry these disadvantages and can still be effective for the target conditions. Piezo-electric polymers: There are attempts to restore blinking using artificial muscles composed of piezo-electric polymers. These systems can be relatively expensive, can require surgical implantation, and can require an external power source.

Examples

Force needed to open the eye in paralytic ptosis was measured to range between 1-3 g in a prior study (Houston K E, Tomasi M, Yoon M, Paschalis E I. A Prototype External Magnetic Eyelid Device for Blepharoptosis. *Transl Vis Sci Technol* 2014; 3:9). Preliminary data for the rotary system shows that a ½×½ cylindrical NdFeB N52 magnet and a three magnet (⅛ in×⅛ in) N52 lid array can deliver the required magnitude of magnetic force to open the lid at a distance of 10 mm to 20 mm between the two magnets (see FIG. 4). The measured maximum force at 20 mm separation distance was approximately 3 grams of lift and repulsion. A trial in a human subject showed passive opening and closing of the lid.

Figure 4:
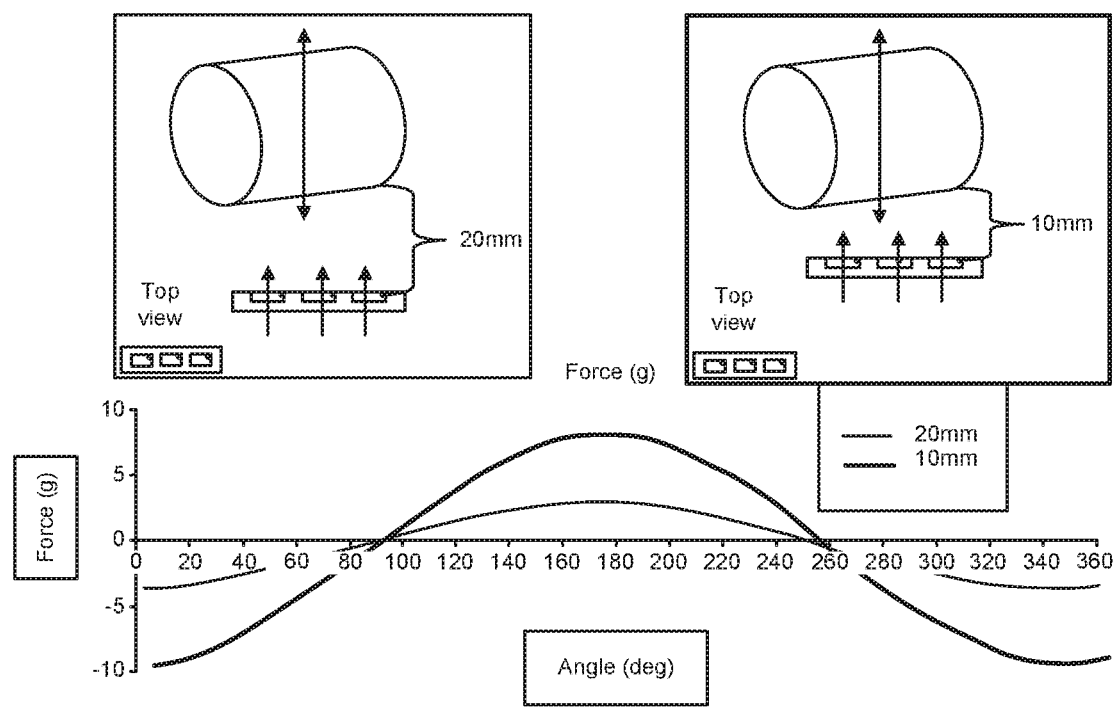
FIG. 4 is a rotary magnet force diagram showing example laboratory force measurements, for an example implementation, of the attractive (positive values) and repulsive (negative values) plotted against frame magnet rotation angle for array to frame magnet distances of 20 mm (red) and 10 mm (blue) when the poles of the magnets are aligned, as shown in the top panels of the figure. Benchmark rotary magnet force measurements show attractive (positive values) and repulsive (negative values) plotted against frame magnet rotation angle for a 12.7 mm×12.7 mm cylindrical magnet with polarization perpendicular to the axis of the cylinder and array to frame magnet distances of 20 mm (red) and 10 mm (blue), as shown in the top panels. Such a system meets the mean force requirements (e.g., 1-3 grams at 10 to 20 mm distance) to open and close the lids.

In a prior experiment, a 3×2×1 mm N52 magnet array in PDMS was mounted on a laboratory scale 10 mm from a cylindrical 12.7×12.7 mm N52 magnet. The cylindrical magnet was rotated by a servo motor in 5 degree increments while changes in force were measured with the scale. The force generated ranged from ~−9 g (repulsion) to +9 g, as shown in FIG. 4. The experiment was repeated with a 20 mm separation finding a range of ~+/−3 g of force. The force of the effective MLP in prior clinical studies, which used a 12.7×12.7 mm cylinder polarized through the axis positioned perpendicular to the frontal plane, was 1 g at a separation of 20 mm, suggesting the prototype rotatable system would provide sufficient force to elevate the lid at ⅔ the total power of the system. Eyelid closure (in total paralysis) can require relatively less force than that needed to elevate the lid because closure can be assisted by gravity and the weight of the lid array. Therefore the prototype rotatable system can provide sufficient force to close the eyelid at <⅔ the total power of the system.

Figure 7A:
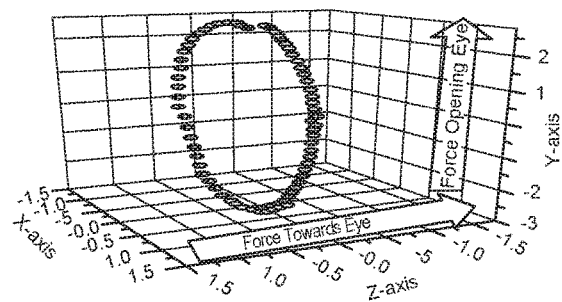
FIG. 7A is a graph describing the magnetic forces exhibited during operation during an experiment using an example device.
Figure 7B:
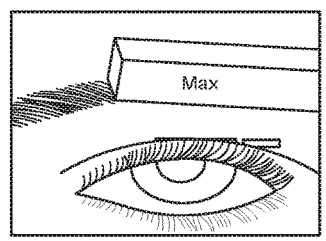
FIG. 7B is a picture showing the eyelid when an example permanent magnet is imparting maximum upward force on the micromagnetic array.
Figure 7C:
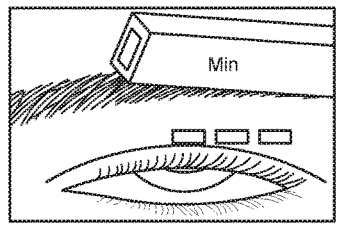
FIG. 7C is a picture showing the eyelid when an example permanent magnet is imparting minimum upward force on the micromagnetic array.
Figure 7D:
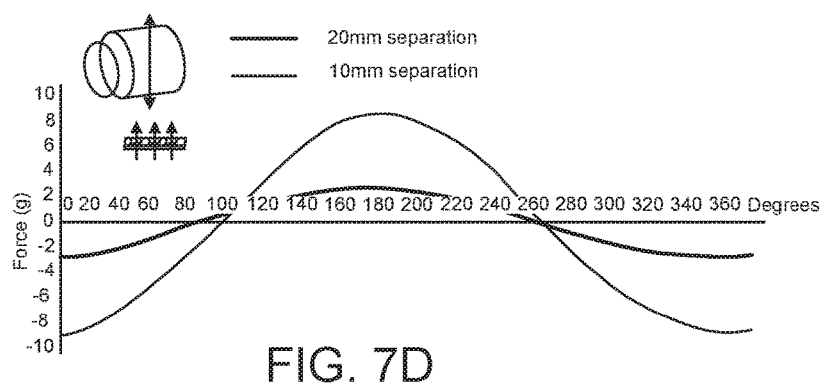
FIG. 7D is a graph showing the force imparted by the permanent magnet throughout the range of rotation of the permanent magnet.
Figure 8:
FIG. 8 is a table showing the experimental results for each of the four test subjects when the device was tested.

Additional testing of an example implementation in human subjects (3 with ptosis, 1 normal) has confirmed that the angular translation can indeed adjust the position of the upper eyelid. In an experiment, the permanent magnet was operated, and three of the four subjects exhibited more than 1 mm of difference in interpalpebral fissure (IPF) (mean 2.5 mm±1.5, range 0.45 to 2.9 mm), suggesting the approach is feasible to adjust lid position in the majority of patients. FIG. 7A shows a plot of 3-D modeling of forces during rotation of the permanent magnet. The largest forces are in the y-axis (vertical). The dark blue, red, and orange areas represent repulsion, whereas the yellow, green and light blue represent attractive forces. FIG. 7B shows the eyelid position when the permanent magnet is oriented to provide maximum y-axis force, corresponding to the junction of yellow and green in FIG. 7A, and FIG. 7C shows the eyelid position when the permanent magnet is oriented to provide minimum y-axis force, corresponding to the junction of light and dark blue in FIG. 7A. FIG. 7D is a graph demonstrating that rotation of the cylindrical diametrically polarized spectacle magnet resulted in ±9gf on the lid magnet at 10 mm which provides a range of adjustment for the population. The results of this experiment for each of the test subjects are detailed in FIG. 8.

Although a few variations have been described in detail above, other modifications or additions are possible. For example, the current subject matter can be utilized by a cornea specialist, ocular plastic surgeon, neuro-ophthalmologist, and/or an optometrist. The current subject matter can be applied to patients having conditions causing lagophthalmos: trauma (burn and physical), and Guillain-Barré related bilateral lagophthalmos; conditions causing ptosis: myasthenia gravis, congenital ptosis, and blepharospasm (dystonia). In some implementations, the device (array) can be adapted for surgical implantation in the lid. The lid magnet polymer can be bio inert. The current subject matter can be mounted on vision testing devices (e.g., visual fields machines, slo, slit lamp) to allow better examination of the eyes (e.g., for patient with ptosis). Another implementation could be in research, where blink rate is precisely controlled to investigate for example, dry eye disease.

The current subject matter can be used to temporarily treat ptosis, which is impeding visual field testing or ocular imaging such as OCT or fundus photography, as part of the testing device. Rather than building into a spectacle, the rotary magnet systems can be built into or attached to the forehead rest. The blink may be automated to prevent desiccation while being synchronized with the imaging system to obtain the best image.

The subject matter described herein provides many technical advantages. For example, the current subject matter is small and portable, requires substantially less power than electromagnets and other approaches, and could be programmed to blink the eyelid occasionally to prevent ocular surface desiccation and can be applied non-surgically or surgically, according to treatment requirements. The current subject matter can include an arrangement of a rotary or translational static magnetic system that can require minimum energy conversion. Unlike some electro-magnets, static (e.g., permanent) magnets can be small, generate strong magnetic force (e.g., net 1.3 Tesla), widely available and inexpensive, do not require an external power source, and do not generate heat. In order to change polarity to open and close the eye, a static magnet can be rotated using an energy efficient motor (e.g., stepper, servo motor or any type of motor/actuator). Compared to electromagnets (which can be excessively heavy and generate heat), such motors can be small enough to be mounted on glasses, do not generate heat, consume minute electrical power, and can run on a 9 v battery controlled with a portable digital controller. Some servo motors can be quiet for portable use. An advantage of some implementations of the present device is that it may not require the use of a similar-in-performance electromagnets, which may not be feasible in a portable application.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

REFERENCES

1. Houston K E, Tomasi M, Yoon M, Paschalis E I. A Prototype External Magnetic Eyelid Device for Blepharoptosis. *Transl Vis Sci Technol* 2014; 3:9.
2. Lipson D, Lelli G J, Rosenblatt MI, Rao R, Nissanka N. Magnetic Control of Eyelid Position. In: U.S. P (ed). United States; 2013 (pending).
3. Senders C W, Tollefson T T, Curtiss S, Wong-Foy A, Prahlad H. Force requirements for artificial muscle to create an eyelid blink with eyelid sling. *Archives of Facial and Plastic Surgery* 2010; 12:30-36.
4. Cyrot M, Decorps M, Dieny B, et al. Magnetism: Materials and Applications. In: du Tremolet de Lacheisserie E, Gignoux D, Schlenker M (eds): Springer; 2005.

5. Ganz R A, Peters J H, Horgan S, Bemelman W A, Dunst C M, Edmundowicz S A. Esophageal sphincter device for gastroesophageal reflux disease. *N Engl J Med* 2013; 368:719727.
6. de Negreiros W A, Verde M A, da Silva A M, Pinto L P. Surgical and prosthetic considerations to rehabilitate an ocular defect using extraoral implants: a clinical report. *Journal of Prosthodont* 2012; 21:205-208.
7. Paschalis E I, Chodosh J, Sperling R A, Salvador-Culla B, Dohlman C H. A novel implantable glaucoma valve using ferrofluid. *PloS one* 2013; 28:e67404. doi: 67410.61371/journal.pone.0067404.
8. Houston K E, Tomasi M, Yoon M, Paschalis E I. A prototype external magnetic eyelid device for blepharoptosis. *Transl Vis Sci Technol* 2014; 3.
9. FDA. 510(k) Summary of Safety and Effectiveness, Tegaderm, 3M Medical Products Division. U.S. Food and Drug Administration; 1997.

What is claimed is:

1. A device comprising:
    a frame configured to be worn adjacent an eye region of a wearer;
    a rotatable housing coupled to the frame; and
    a permanent magnet coupled to the rotatable housing and including a first surface having a first static magnetic polarity and a second surface having a second static magnetic polarity opposite the first static magnetic polarity, the rotatable housing arranged to rotate the permanent magnet between a first position orienting the first surface towards the eye region of the wearer and a second position orienting the second surface towards the eye region of the wearer.

2. The device of claim 1, wherein the device further includes a servo motor, a stepper motor, a linear motor, a micro-fluidic motor, a hydraulic motor, or a knob.

3. The device of claim 1, further including a micromagnetic array adhered to an eyelid of the wearer and surrounded by an optically clear polymer.

4. The device of claim 3, wherein the optically clear polymer includes a silicon-based organic polymer.

5. The device of claim 3, wherein the optically clear polymer includes polydimethylsiloxane (PDMS).

6. The device of claim 1, wherein the permanent magnet includes a neodymium magnet.

7. The device of claim 1, further comprising a memory controller unit coupled to a motor and including a memory and a controller, the controller configured to access a predetermined rotation schedule protocol included in the memory and to control the rotation of the permanent magnet based on the predetermined rotation schedule protocol.

8. The device of claim 7, wherein the predetermined rotation schedule protocol includes instructions to actuate the motor every 2 seconds, every 3 seconds, every 4 seconds, every 5 seconds, every 6 seconds, every 7 seconds, every 8 seconds, every 9 seconds, every 10 seconds, every 11 seconds, every 12 seconds, every 13 seconds, every 14 seconds, every 15 seconds, every 16 seconds, every 17 seconds, every 18 seconds, every 19 seconds, every 20 seconds, every 10 hours, or every 20 hours.

9. The device of claim 7, further comprising an input coupled to the rotatable housing and configured to control the rotation of the permanent magnet when the input is activated by a user.

10. The device of claim 9, wherein the input is a button, a knob, or a switch.

11. A method comprising:
    providing a frame configured to be worn adjacent an eye region of a wearer, a rotatable housing coupled to the frame, and a permanent magnet coupled to the rotatable housing and including a first surface having a first static magnetic polarity and a second surface having a second static magnetic polarity opposite the first static magnetic polarity, the rotatable housing arranged to rotate the permanent magnet between a first position orienting the first surface towards the eye region of the wearer and a second position orienting the second surface towards the eye region of the wearer; and
    actuating a micromagnetic array adhered to an eyelid of the wearer by rotating the permanent magnet between the first position and the second position to move the eyelid.

12. The method of claim 11, further providing a servo motor, a stepper motor, a linear motor, a micro-fluidic motor, a hydraulic motor, or a knob.

13. The method of claim 11, wherein the micromagnetic array includes a magnet surrounded by an optically clear polymer.

14. The method of claim 13, wherein the permanent magnet includes a neodymium magnet.

15. The method of claim 11, further comprising providing a memory controller unit coupled to a motor and including a memory and a controller, the controller configured to access a predetermined rotation schedule protocol included in the memory and to control the rotation of the permanent magnet based on the predetermined rotation schedule protocol.

16. The method of claim 15, further comprising providing an input coupled to the rotatable housing and configured to control the rotation of the permanent magnet in response to activation of the input by a user.

17. The method of claim 15, wherein the input is a button, a knob, or a switch.

18. The method of claim 11, wherein the micromagnetic array is adhered to the eyelid of the wearer using a hydrocolloid adhesive provided over a top surface of the micromagnetic array.

19. The method of claim 11, wherein the predetermined rotation schedule protocol includes instructions to actuate the motor every 2 seconds, every 3 seconds, every 4 seconds, every 5 seconds, every 6 seconds, every 7 seconds, every 8 seconds, every 9 seconds, every 10 seconds, every 11 seconds, every 12 seconds, every 13 seconds, every 14 seconds, every 15 seconds, every 16 seconds, every 17 seconds, every 18 seconds, every 19 seconds, every 20 seconds, every 10 hours, or every 20 hours.

* * * * *